United States Patent [19]

Beck

[11] Patent Number: 5,070,543
[45] Date of Patent: Dec. 10, 1991

[54] METHOD AND MEANS OF SURGICAL NEEDLE PROTECTION

[76] Inventor: William C. Beck, 110 Vista Dr., Sayre, Pa. 18840

[21] Appl. No.: 310,821

[22] Filed: Feb. 14, 1989

[51] Int. Cl.⁵ ............................................. A41D 13/10
[52] U.S. Cl. ................................................ 2/163; 2/21
[58] Field of Search ................... 2/16, 21, 159, 160, 2/161 R, 163, 168; 128/879, 880

[56] References Cited

U.S. PATENT DOCUMENTS

| | | | |
|---|---|---|---|
| 1,010,283 | 11/1911 | Loy | 2/163 |
| 1,066,480 | 7/1913 | Finlay | 2/21 |
| 2,335,320 | 11/1943 | Swietck | 2/163 |
| 2,725,570 | 12/1955 | Penna | 2/163 |
| 3,164,841 | 1/1965 | Burtoff | 2/16 X |
| 3,511,242 | 5/1970 | Agnone | 2/21 X |
| 3,593,803 | 7/1971 | Ibach | 2/160 X |
| 3,633,216 | 1/1972 | Schonholtz | 2/168 |
| 4,127,222 | 11/1978 | Adams | 2/21 X |
| 4,272,849 | 6/1981 | Thurston et al. | 2/16 |
| 4,681,012 | 7/1987 | Stelma et al. | 2/160 X |
| 4,774,727 | 10/1988 | Jackson | 2/161 R |
| 4,858,245 | 8/1989 | Sullivan et al. | 2/163 X |
| 4,864,661 | 9/1989 | Gimbel | 2/161 R X |
| 4,873,998 | 10/1989 | Jayner | 2/16 X |

Primary Examiner—Werner H. Schroeder
Assistant Examiner—Sara M. Current
Attorney, Agent, or Firm—Ralph R. Barnard

[57] ABSTRACT

A method and specifically constructed surgical gloves and glove parts for protecting a user of a surgical instrument from protrusion through his own skin by the instrument he is manipulating to cut or suture a patient comprising the following steps:
 a) the user wearing surgical gloves
 b) adding a impervious protective pad to the especially selected surface area of the surgical gloves at a location in the hand or hands of the user where it is probable that the use or surgical procedure would result in the penetration by the surgical instrument through the skin of the user through the surgical glove or gloves.

18 Claims, 3 Drawing Sheets

Fig. 6a
Fig. 6b
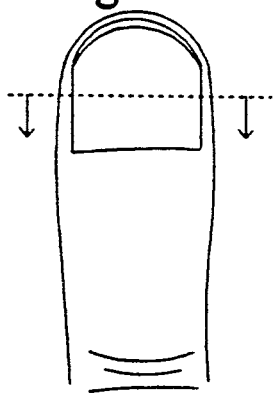
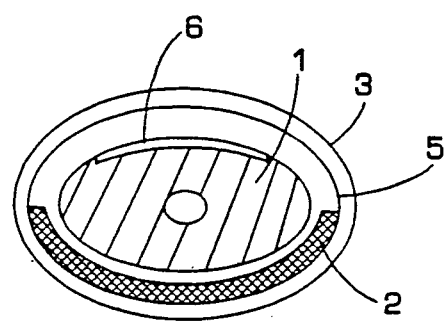

METHOD AND MEANS OF SURGICAL NEEDLE PROTECTION

FIELD OF THE INVENTION

This invention relates generally to the field of surgical gloves used for the purpose of preventing the transmission of infections in the process of any surgical or suturing procedure conducted on a patient and more particularly to the prevention of penetration of surgeons skin during the process of manipulation of a sharp surgical instrument.

BACKGROUND OF THE INVENTION

In an article entitled "Surgical Glove Perforation" Br. J. Surg. 1988, Vol 75, October, 966-968, it was stated "the surgical glove was introduced in 1889 by Halsted to protect his nurse assistant, Caroline Hampton, from dermatitis caused by mercuric chloride used for Listerian antisepsis. It was soon realized that sterile gloves provided a barrier between the surgeons, hands and the patient and could thus reduce iatrogenic infection. Lord Moynahan pioneered their use in the UK and the wearing of gloves during surgery has long been standard practice.

Modern surgical scrub technique dramatically reduces the bacterial counts on surgeons remain. It has often been stated that when glove perforation occurs, bacteria can escape and contaminate the wound, thus leading to an increased risk of wound sepsis. For this reason surgeons change their gloves during an operation when perforation has occurred although supporting bacteriological evidence is "scant". While the technology of surgical gloves has made tremendous advances in terms of quality of the touch retained by the user as well as a high residual manipulative capability of the hand and fingers including wearer comfort, the current American (voluntary) Standard ASTM D3577-78 permits new gloves to have ½% holes. Even more hazardous, at the end of operations 10-50% of surgeon's gloves are reported to have holes (Church, J., Sanderson, P.: Surgical Glove Punctures. Journ. Hosp. Infect. Control 1980, 1:84).

In the Br. J. Surg. publication identified hereinabove, the authors also reported on a study to investigate the incidence and significance of surgical glove perforation, bacterial contamination of surgeons' hands and gloves before and after operation was measured and the gloves tested for damage. Perforations were found in 74 of 582 gloves (12.7 per cent) and occurred in 34.5 per cent of operations. Glove perforation did not influence bacterial counts on the surgeons' hands or on the outside of their gloves. A separate clinical study of 100 adult hernia repairs gave no evidence that perforation increased wound sepsis. After standard clinical significance to the patient, but their high incidence should alert surgeons to the need for protection against pathogens transmissible during surgery, such as hepatitis B and the human immunodeficiency virus. Protection of the surgeon is an indication for preoperative change of damaged gloves throughout the course of the operation or surgical procedure. Increased incidence of risk for the persons performing activities with respect to persons having dreaded communicable diseases which are transmitted via the bodily fluids, make protection of the user of sharp instruments such as surgical knives and/or needles a major concern and has emphasized the need for the proper use of surgical gloves. Proper use is also particularly important for the person using the surgical instrument or conducting any activity inside the body of the infected or potentially infected patient and particularly when the surgical or protective gloves are penetrated and at the same time the user of the gloves is provided with little protection from such sharp objects as a needle, knife or scissor's edge, etc. While no evidence has yet established that a surgeon can contract the AIDS virus by penetrating his surgical glove and his own skin with a needle or similarly penetrating instrument, there is an overwhelming concern about the possibility which is to significant to ignore. The teachings of the present invention respond to this concern.

The problem with holes in surgical gloves has been studied by others in addition to the report sited hereinabove, one such report is by H. Matta, et al, entitled "Does wearing two pairs of gloves protect operating theatre staff from skin contamination?", pages 597-598—BMJ volume 290—Sept. 3, 1988. Therein, ten surgeons and nine scrub nurses in a surgical unit wore two pairs of gloves during general surgical operations on 144 consecutive patients. The gloves were tested at the end of the operation by a recognized method detecting perforation. The following table was reported: Numbers of punctures detected at different sites in 728 outer and inner gloves

|  | Left hand | | Right hand | |
|---|---|---|---|---|
|  | Outer glove | Inner glove | Outer glove | Inner glove |
| Thumb | 6 |  | 1 |  |
| Index finger | 33 | 5 |  |  |
| Third finger | 6 | 1 | 4 | 1 |
| Fourth finger | 3 |  | 2 | 1 |
| Fifth finger | 1 |  |  |  |
| Palm | 16 | 6 | 5 | 1 |

It is notable that three quarters of the perforations have occurred on the index finger of the left hand. It may therefore be presumed, particularly if both gloves frequently contained holes, that these were punctured holes produced by sharp instruments rather than tears or other violence; or, part of the permitted quality level original holes in the glove.

While this reported study confirms that wearing two pairs of surgical gloves confers some protection against contamination of the surgeons or nurses from the patients tissue and fluids, a very significant aspect of the results is that it identifies to a substantial degree where the glove punctures are located. For example, the non-dominant hand for the user of surgical instruments would be the left hand and therein is were the largest number of punctures are identified. That fact and the location of the punctures in the categories as set forth in the table leads to the conclusion that while all of the punctures or holes in the gloves are not the result of self inflicted punctures by the user through the use of the surgical instrument, many are. The locations of those punctures are identified and give the user an idea of where they may be causing punctures of the surgical gloves as well as the invasion of their own skin. The information described above is confirmed by an article entitled "Risk to Surgeons: A Survey of Accidental Injuries During Operations", Br. Journal of Surg. April 1988, pp:314-315.

SUMMARY OF THE INVENTION

It was this context that the present inventor conceived and discovered that he could use a shield at particular locations in the surface area of surgical gloves and give protection to the user of the surgical instruments in relation to the concern of protecting himself from contamination by bodily fluids including tissue fluids of the patient through the skin of the surgeon while at the same time protecting the patient from the contamination that might result from the hands of the surgeon through self inflicted punctures by the surgeon. Moreover, the present inventor discovered that the surgeon or user of surgical instruments could use the prior art technique of empirical evidence to determine for his particular method of handling the instruments doing certain surgical procedures where it was most likely that he would need protection from self inflicted punctures of his surgical gloves and of his own skin. Each surgeon or practitioner can utilize the method of the teachings of this invention by deciding for themselves where on his fingers or hands he needs protection and utilize gloves having shields at special locations, as well as certain categories of protection. For example, looking at the table shown the surgeon would want a shield on the palmar side of the index finger of his left hand such that the shield placed there would be placed in the glove or glove system (in two gloves or one cot and a glove). The shield would be impervious to penetration by sharp instruments such as a needle. The limitations on how many shields would be on any surgical glove would be determined by the need of the particular surgeon and the adverse effect of the use of each shield on the dexterity and touch required by the surgeon. For example, for a large number of surgeons over a wide number of surgical procedures the surgeon might, if he were right handed, rely on one shield on the palmar side of the index finger of the left hand. Alternatively, the same surgeon might want a shield on the palmar side of the adjacent third finger as well. Through empirical evaluation each surgeon might make his own decisions on his design of his throw away surgical gloves, very much like a big league baseball hitter might have his own special selection of bats for special hitting circumstances. However, in fact it may be that the throw away surgical gloves used by the largest number of users will be all of the same design.

In view of the above, the present invention teaches a new and improved method and means for protecting the user of surgical instruments from self inflicted perforations of both the surgical glove and the protective skin of the user, from contamination from the bodily fluids of the patient whose fluids and tissue might contain infectious pathogens and at the same time protecting the patient from being contaminated by contaminants from the surgeon's hands.

It is still another object of the present invention to teach a method in which a user can select surgical glove type means to protect himself against self inflicted penetrations of his skin and contamination from the body fluid or tissue of the patient during the use of surgical instruments on a patient.

It is an additional object of the present invention to teach the user the type of shield glove combinations which he may select or through his requirements, manufacture might make to render the level of protection to the user which he requires commensurate with the requirement of the user to maintain the kind of manipulative freedom for his hands and fingers as well as feel in conducting all the various types of surgical procedures that are to be required of the surgeon user over the course of time.

Objects of the present invention are accomplished by each user determining for his own purposes which parts of his or her own non dominant hand or both hands might be a probable location of self inflicted penetration through both the surgical gloves and his skin and essentially determining for him or herself where a shield would be located in the surface of the surgical gloves in a location which would protect him but not decrease his ability to conduct the surgical procedure.

BRIEF DESCRIPTION OF FIGURES

These and other objects, features and advantages of the present invention should become apparent from the following description when taken in conjunction with the accompanying drawings in which:

FIG. 6a, shows a user's index finger showing where the cross section of index finger of 6b is taken.

FIG. 6b, shows the cross section of the index finger of 6a when that index finger is also the user index finger as shown in 5b.

DETAILED DESCRIPTION

In these days of AIDS-phobia, several devices have been suggested to keep the surgeon from pricking himself with his suture needle. These include chain-mail armor, the heavy gloves worn by the oystermen, and other protective materials. Almost invariably it is the palmar surface of the distal phalanx of the left index finger (in right-handed surgeons) which is injured. Had he but grown his fingernail on the palmar side of his finger, he would have escaped this hazard. A whole, impervious glove or pair of gloves is over-protective, cumbersome, and unnecessary.

Such an approach was described in the Medical Tribune on page 22, Thursday, July 14, 1988. Therein, a new protective surgical glove of a surgeon by the name of Arnold Seid, M.D. was described consisting of 3 layers of a "high-tech" tightly woven nylon fabric sandwiched between two layers of latex rubber. However, as shown such sandwich is shown as covering the palm side of the whole hand, all the fingers and thumb. It is "overkill" to protect the dominate hand or both hands when only a very small area is at risk. This reduces the effectiveness and dexterity of the surgeon.

The teachings of this invention relate to shields selectively placed on the glove or fingercot where protection is needed, all toward the end of maintaining the manipulative quality dexterity quality and feel quality, of the user's surgical gloved hand to the optimum level.

It seems almost too simplistic to suggest that the surgeon wear a thimble, even one with the back (over the nail area) cut away. This would have disadvantages, not the least being that it could slip off and than be hard to locate in body cavities.

Figure 1:
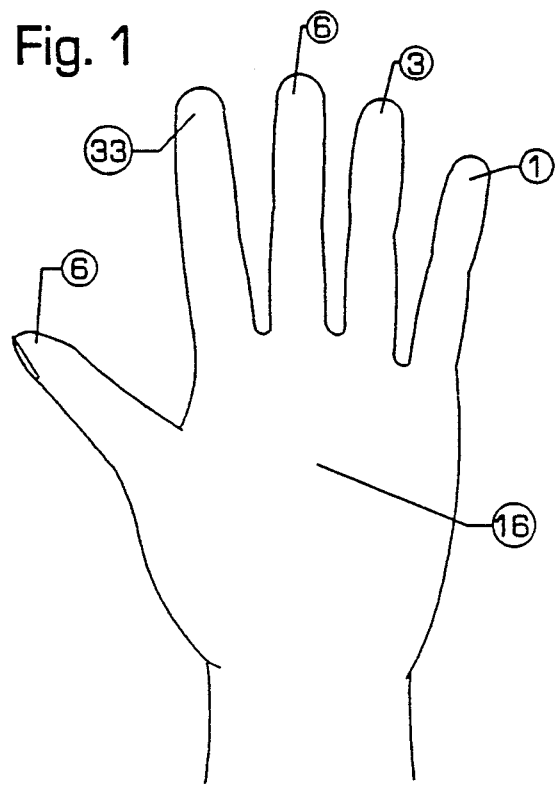
FIG. 1, shows the result of one empirical study on the non-dominant left hand of a surgeon in diagramatic form in that the left hand, thumb and fingers show the numbers of punctures found in surgical gloves after known procedures were conducted and tests were made of the glove. The data is taken from the table and scientific report identified hereinabove as pages 595-596, BMJ volume 290, Sept. 3, 1988.

FIG. 1, shows the result of one empirical study on the non-dominant left hand of a surgeon in diagramatic form in that the left hand, thumb and fingers show the number within circles of punctures found in surgical gloves after known procedures were conducted and tests were made of the glove. The data is taken from the table and scientific report identified hereinabove as pages 595-596, BMJ volume 290, Sept. 3, 1988. Given the fact that some of holes or punctures identified in FIG. 1 are latent to the glove many result from the course of surgical operations. It has been reported that at the end of the operations that 10-50% of the surgeons gloves have holes. The theory of the present invention is that the locations of the holes or punctures caused by surgical instruments during an operation can be identified for classes of operational procedures as well as users or surgeons and an shield (impervious to sharp instruments) may be placed in those areas of the surgical glove by adhering the shield to the surgical glove material at very selected locations using data not unlike that shown in FIG. 1. This can be done by using small impervious shields and not render the surgical gloves ineffective in terms of all of the qualities it must have in terms of touch, feel and manipulation etc.

Figure 2:
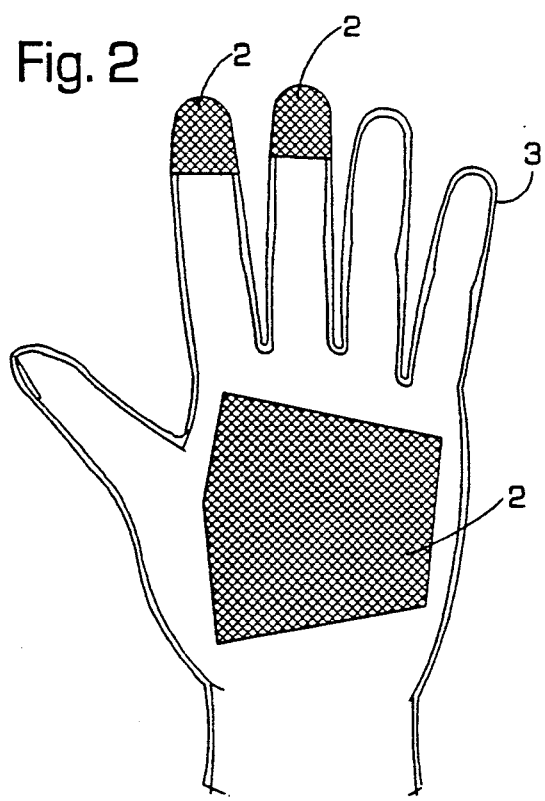
FIG. 2, shows the application of a shield on the surface of the outer surgical glove above the palm the index and/or the third finger of the left hand.

By way of example, FIG. 2, shows the application of an impervious shield 2 (of the types described herein) on the surface of the outer surgical glove 3 above the palm, the index and/or the third finger of the left hand 1 in accordance with the teachings of the present invention, the shape and size of the shield in the palm can vary with the need for protection and the effect of the shield pad on the other qualities. The shield would be adhered to the surgical gloves using standard techniques. For a particular user or particular procedure the location of the shields would vary.

Figure 3:
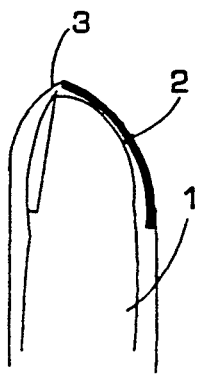
FIG. 3, shows the application of a shield on the inner surface of an inner surgical glove of one of a selected finger of the selected hand above and adjacent the palm of that finger.

FIG. 3, shows the application of a shield on the inner surface of an inner surgical glove of one of a selected finger of the selected hand covering the palmar side of the distal phalanx of the finger.

Figure 4:
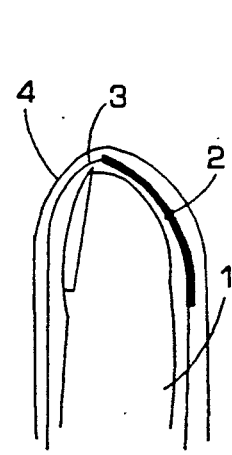
FIG. 4, shows the application of a shield on the outside surface of the inner surgical glove of a selected finger of a selected hand above the palm of that finger.

FIG. 4, shows the application of a shield 2 on the outside surface of the inner surgical glove 3 of a selected finger of a selected hand covering the palmar side of the distal phalanx that finger with the glove finger 4 of the outer glove as shown.

Figure 5A:
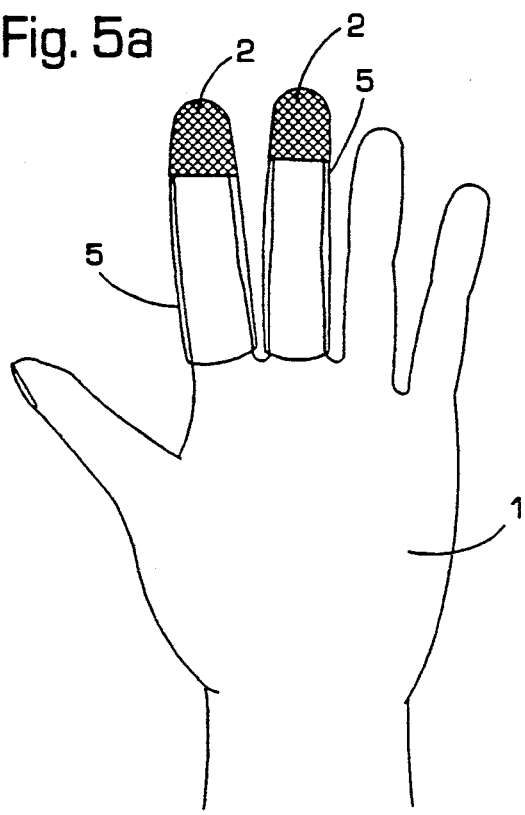
FIG. 5a, shows the application of fingercots on a left hand of a surgeon, which fingercots have a shield on the outside thereof against the palm of the index and/or third finger.

FIG. 5a, shows the application of fingercots 5 on a left hand of a right handed user, fingercots 5 have a shield 2 on the outside thereof against the palmar side of the index and/or third finger. However, the shield 2 could have been on the inside of fingercot 5. Although two fingercots 5 each with shield 2 are shown, it is clear tat more or/less fingercots can be used with shields if desired based on the user and the procedure.

Figure 5B:
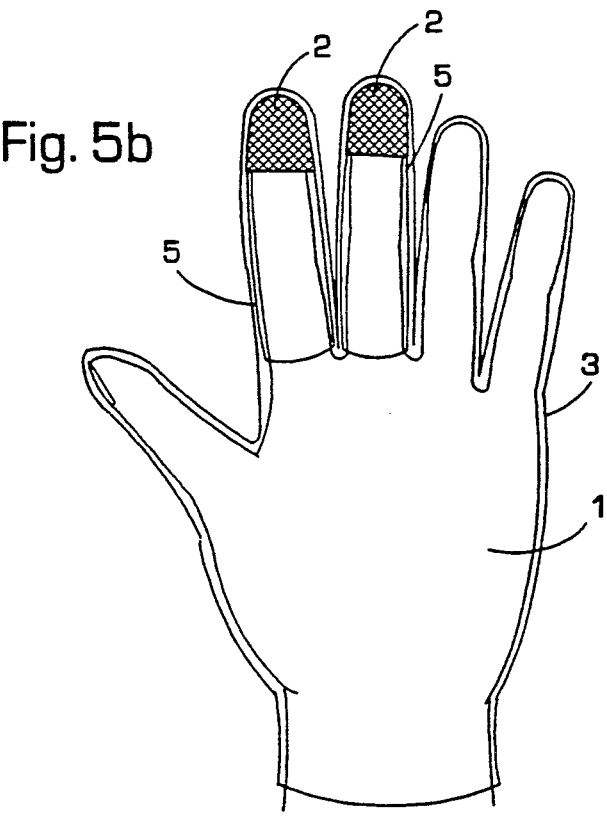
FIG. 5b, shows the fingercot or fingercots of FIG. 5a being worn underneath an outer surgical glove.

FIG. 5b, shows the fingercot or cots of FIG. 5a being worn underneath an outer surgical glove 3.

As described above the number of fingercots 5 with shields 2, which can be used can vary and one cot could be used on the thumb, moreover a shield could be adhered to the palm of the glove at a particular location and size as required.

FIG. 6a shows a user's index finger showing where the cross section of the index finger of FIG. 6b is taken.

FIGS. 6b shows a cross section of FIG. 6a when the index finger is also the index finger of the user as shown in FIG. 5b. The user's fingernail 6 is shown. The cross section of the finger 1 with bone is shown Impervious shield 2 is shown on the palmar side of the finger 1 and the fingercot 5 material is shown and the surgical glove finger material 3 is shown.

It is just as easy to wear a short fingercot covering the two distal phalanges with or without a rolled top, wherein a shield which is impervious to sharp instruments such as a needle, knife or scissor's etc., and made of one of many kinds of materials discussed herein elsewhere, such as an artificial nail like to those obtainable at any cosmetic counter. The short fingercot may be worn so that an oversized nail-like shield was on the inside, on the volar aspect of that finger; then the prior art surgical glove could be slipped over it. Given empirical evidence of the general type or specific empirical evidence for the particular surgeon for the particular type of surgical procedure, the surgeon's safety would probably be served by wearing a fingercot with a shield i.e. artificial nail on both the index finger and the adjacent third finger with something like an artificial nail covering the palm of the index finger and the adjacent third finger of the non-dominant hand with the surgical gloves pulled there over.

The artificial nail, or protective material, could be attached directly onto the surface on the surgical glove while it was still on its mold. This, however, this could only be done to a powder-free glove. It could present special difficulty, as two convex curvatures would have to be in apposition. The process can be more simply accomplished with a separate sterile fingercot beneath the glove. The plastic or similar material would be applied to the latex cot as to be next to the wearer's skin, and the cot then everted when removing from the mold. It is easy to slip the glove over this fingercot with the shield. Thus, the distal two joints of these vulnerable fingers would be double-gloved. This in itself would afford added protection against holes developing, without the need of double-gloving.

Recognizing that the palmar shield in the form of a nail on the palmar side of the index finger might reduce the surgeon's tactile sensibility, the surgeon might well wear the protective shield on the left hand or the non-dominant hand since he predominately palpates with the distal phalanx of the dominant hand.

The shield referred to herein can take many forms, the most readily available for some would be an artificial fingernail aquired from any of the sources of cosmetic goods as sold in retail cosmetic stores and an adhesive may be used to adhere it to a location on the latex finger cot or the latex surgical glove so that the fact that the shield is impervious to the sharp objects such as needles, knife edges or scissor edges, etc. will prevent the glove surfaces, fingercot surfaces or the skin of the user from being penetrated during surgical procedures.

The shield can be any of a variety and can be made of any material which is impervious as required and at the same time is compatible with being sterilized along with the latex material used in the surgical fingercots and the surgical gloves.

Examples would be many plastics and natural materials such as any metal etc. For example, both Allied-Signal and Du Pont have developed a new kind of ultra high molecular weight polyethylene material which Allied-Signal calls Spectra Shield and Du Pont Inc. calls their material Kevlar 29. For further description see an article entitled "Step aside, Superman" appearing in Forbes magazine Feb. 6, 1989, pages 124-126. In any event the shield may be made from layers of parallel fibers, each layer of fibers laying parallel being laid at right angles. The problem of making a shield purposes of this application would be less demanding than that for the bullet proof shields for which these two company's offer.

The commercially available materials identified above are but one example of materials that could be used to practice the invention, but what ever material is used, that material must be capable of sterilization.

During surgical operations, surgeons often produce needle-pricks while sewing tissues. Most of these occur on the distal phalanx, palmer surface of the surgeon's non-dominant hand. This invention is designed to protect this part of a surgeon's finger. While the device world primarily be worn beneath the glove on the index finger, it could also be worn on any finger so exposed. It also would provide that finger with double protection of a double glove, minimizing the effect of needle-pricks which penetrate the outer glove.

The device consists of a latex fingercot (finger of a glove either with or without a rolled top), to which has been affixed a heavy or dense material which sufficiently resistant to be imperious to penetration by pointed instruments such as needles. This could be either made of plastic, metal, or merely a thick rubber pad. Tightly woven textiles, if impervious to surgical needles, could also be employed. These would be applied to either the inside or the outside of the fingercot, i.e. against the wearer's skin or on the outer surface. As used herein, to describe the teachings of the present invention, the fingercot may be considered as glove means or a glove part.

The impervious material might merely cover the pad of the distal phalanx or surround the major part of this finger part.

A similar pad could also be applied to the more proximal phalanx, affording it similar protection.

The device would usually be sterilized and usually worn under the surgical glove and therefore donned first. However, it could be worn on or over the glove, or even worn on a bare hand.

This device could be worn throughout an operation, or donned when the suturing process would begin.

The device would have little if any effect on the sensitivity of the surgeon's palpatory ability as it would be worn on the non-dominant hand (left hand of the right handed surgeon). Most palpation is done by the dominant hand.

As used herein, the identification of the user as a surgeon is intended to identify any user of a sharp surgical instrument doing any procedure where protection of the user from penetration of the skin allowing pathogens etc. to invade beyond the protective skin of the user. The non-dominant hand means the hand of the user which is not the one the user chooses to use for his manipulative operation of the surgical instrument. In a right handed person it would be the left hard and in the left handed person it would be the right hand and in an ambidextrous person it would be the hand the user would not be using in a primary fashion while manipulating the surgical instrument.

A fingercot means that is a short finger cover often of latex vinyl or and other similar material which medical people use to protect a single finger during probing the human body.

The teachings of the present invention include the method of use of a shield, impervious to sharp instruments on selective locations of a surgeon's hand and fingers when he is using a sharp instrument so that the surgical instrument will not penetrate the skin of the user, wherein the location of the shield is being determined by what the surgeon and the supplier of the surgical shield latex glove combination necessary in certain types of procedures on the patient for the protection of the user against penetration of his skin and invasion of the user by harmful pathogens exemplified by Hepatitis B virus and the AIDS virus.

Manufacturers of surgical gloves may utilize the invention to develop standard categories of selective shielded latex glove combinations based on the generalities of needed protection based on the wide similarities for surgical type operations. Moreover, the surgeon's themselves can have surgical gloves designed for them based on their own concern and evaluation. All these decisions will represent a balance between the need for the user maintaining his manipulatively capability, his dexterity, his feel for the preservation of self practices for himself, and the overall need for using surgical gloves for the benefit of the patient.

The foregoing description has been directed to particular embodiments of the invention in accordance with the requirements of the Patent Statutes for the purposes of illustration and explanation. It will be apparent, however, to those skilled in this art that many modifications and changes will be possible without departure from the scope and spirit of the invention. It is intended that the following claims be interpreted to embrace all such modifications.

I claim:

1. A method of protecting a user of a surgical needle, knife or scissor's from injury and resulting infection when manipulating and cutting or suturing an infected patient comprising of steps:
    (a) confirming said user's determination of which hand would not manipulate the sharp surgical instrument and confirming what surfaces of that hand or fingers would be used by him to hold a part of the infected patient to be sutured or cut such that the sharp surgical instrument would be pointed thereagainst;
    (b) said surgeon then selecting surgical gloves to do the cutting or suturing that includes a selective minimally sized shield impervious to the passage of the sharp surgical instruments, such as a surgical needle, therethrough in the surface area of the glove located at least over the entire palmar side of the distal phalanx of the index finger of that hand; and
    (c) donning said gloves.

2. The method of claim 1 wherein there is a selective minimally sized shield impervious to the passage of the sharp surgical instruments therethrough in the surface area of the glove located at least over the entire palmar side of any other finger.

3. The method of claim 2 wherein there is a selective minimally sized shield impervious to the passage of the sharp surgical instruments therethrough in the surface area of the glove over that portion of the palm of the hand most likely to be used in a manner to touch into the needle point during the suturing operation.

4. The method of claim 1 wherein said selective minimally sized shield impervious to the passage of the sharp surgical instrument therethrough in the surface area of the glove located at least over the entire palmar side of the index finger of that hand is provided by a fingercot of latex having a shield therein in the surface area of said fingercot at least over the entire distal palmar portion of the index finger and where the latex glove on that hand is pulled over said fingercot and shield.

5. A fingercot for the non-dominant hand of the surgeon suturing or cutting tissue of an infected patient comprising:
(a) a latex fingercot;
(b) a shield impervious to a sharp protrusion, such as a sharp surgical needle, in the surface of said fingercot located to cover at least the entire palmar surface area of the distal phalanx of the finger to which fingercot is applied.

6. A fingercot for wearing under the latex gloves for the non-dominant hand of the surgeon suturing or cutting tissue of an infected patient comprising:
(a) a fingercot;
(b) a shield impervious to a sharp protrusion, such as a sharp surgical needle, in the surface of said fingercot located to cover at least the entire palmar surface area of the distal phalanx of the finger to which fingercot is applied; and
(c) said fingercot with said impervious shield being adapted to be applied over at least the index finger under a latex glove of the non-dominant hand of a surgeon performing suturing or cutting.

7. Fingercots for wearing under the surgical gloves for the non-dominant hand of the surgeon suturing or cutting tissue of an infected patient comprising:
(a) a first and second latex fingercot;
(b) a shield impervious to sharp protrusion of a surgical needle in the surface of each of said fingercots located to cover at least the entire distal palmar surface area of the finger to which fingercot is applied; and (c) each of said latex fingercots with said impervious shield being adapted to be applied over at least the index finger and adjacent finger under a latex glove of the non-dominant hand of a surgeon performing suturing or cutting.

8. A method of protecting a user of a surgical needle from infection when cutting or suturing an infected patient comprising of steps:
(a) confirmation of said user's determination of which hand would not manipulate the needle and confirming what surfaces of that hand would be used by him to hold a surface to be sutured such that the needle would be pointed thereagainst;
(b) said surgeon then selecting surgical gloves to do the suturing that includes a selective minimally sized shield impervious to the passage of the needle therethrough in the surface area of the glove located at least over the entire palmar surface of the index finger of that hand; and
(c) donning said gloves.

9. The method of claim 8 wherein there is a selective minimally sized shield impervious to the passage of a needle therethrough in the surface area of the glove located over the palmar side of the finger adjacent to the index finger of that hand.

10. The method of claim 9 wherein there is a selective minimally sized shield impervious to the passage of the needle therethrough in the surface area of the glove over that portion of the palm of the hand most likely to be used in a manner to touch into a sharp instrument during the surgical procedure.

11. The method of claim 8 wherein said selective minimally sized shield impervious to the passage of the needle therethrough in the surface area of the glove located at least over the palmar side of the index finger of that hand, is provided by a fingercot of latex having a shield therein in the surface area of the fingercot over the distal palmar portion of the index finger and where the latex glove on that hand is pulled over said fingercot and shield.

12. A method of protecting a user of a surgical instrument from protrusion through his own skin by the instrument when he is manipulating, cutting or suturing a patient comprising the following steps:
a) the user wearing surgical gloves;
b) adding a selective minimally sized shield impervious to the passage of sharp surgical instruments, such as a surgical needle, therethrough to the especially selected surface area of the surgical gloves at a location in the hand or hands of the user where it is probable that the use of said instruments or surgical procedure would result in the penetration by the surgical instrument through the skin of the user through the surgical glove or gloves.

13. The method of the claim 12 wherein said selective minimally sized shield impervious to the passage of sharp surgical instruments, such as a surgical needle, therethrough is added to the surface of the surgical glove or glove part at least at the distal phalanges of the index finger.

14. A method of protecting a user of a surgical needle from infection when cutting or suturing an infected patient comprising the step of adding a selective minimally sized shield impervious to the passage of sharp surgical instruments, such as a surgical needle, therethrough to the distal phalanges of the index and middle finger of a surgical glove.

15. A surgical glove means especially adapted for use in protecting the user when suturing or cutting a patient made by the following method: adding a selective minimally sized shield impervious to the passage of surgical instruments, such as a surgical needle, therethrough to the surface of a surgical glove at each specific location where the user would most probably penetrate his own skin and the surgical glove with a sharp surgical instrument.

16. A surgical glove means especially adapted for use in protecting a user when suturing or cutting a patient comprising:
a) a shield impervious to the passage of sharp surgical instruments, such as a surgical needle, therethrough to be included in the surface of said surgical glove means at each specific location where the user would most probably penetrate his own skin and said surgical glove with a sharp surgical instrument;
b) wherein the location and number of the selective minimally sized shields impervious to passage of sharp surgical instruments therethrough in the surface of said surgical glove is determined by a trade off between the surgical glove remaining usable in terms of its effects on the manipulative, feel and dexterity requirements for the user's hands and the need of the user for having protection from penetration by a sharp surgical instrument at particular locations based on the user's own methods of accomplishing surgical tasks as well as the special requirements of selected surgical tasks.

17. A surgeon's hand protection means especially adapted for use in protecting the user when suturing or cutting a patient made by the following method:

adding a selective minimally sized shield impervious to the passage of surgical instruments, such as a surgical needle, therethrough to the surface of a surgeon's hand protection means at each specified location where the user would most probably penetrate his own skin and the surgeon's hand protection with a sharp surgical instrument.

18. A surgeon's hand protection means especially adapted for use in protecting a user when suturing or cutting a patient comprising:

a) a shield impervious to the passage of sharp surgical instruments, such as a surgical needle, therethrough to be included in the surface of said surgeon's hand protection means at each specific location where the user would most probably penetrate his own skin and said surgeon's hand protection means with a sharp surgical instrument;

b) wherein the location and number of the selective minimally sized shields impervious to passage of sharp surgical instruments therethrough in the surface of said surgeon's hand protection means is determined by a trade off between the surgeon's hand protection means remaining usable in terms of its effects on the manipulative, feel and dexterity requirements for the user's hands and the need of the user for having protection from penetration by a sharp surgical instrument at particular locations based on the user's own methods of accomplishing surgical tasks as well as the special requirements of selected surgical tasks.

* * * * *